(12) United States Patent
Roesner et al.

(10) Patent No.: US 6,633,379 B2
(45) Date of Patent: Oct. 14, 2003

(54) APPARATUS AND METHOD FOR MEASURING THE DEGRADATION OF A TOOL

(75) Inventors: Michael Roesner, Dresden (DE); Manfred Schneegans, Vaterstetten (DE); David Wallis, Dresden (DE)

(73) Assignees: Semiconductor 300 GmbH & Co. KG, Dresden (DE); Infineon Technologies AG, Munich (DE)

( * ) Notice: Subject to any disclaimer, the term of this patent is extended or adjusted under 35 U.S.C. 154(b) by 89 days.

(21) Appl. No.: 09/877,531

(22) Filed: Jun. 8, 2001

(65) Prior Publication Data

US 2002/0186370 A1 Dec. 12, 2002

(51) Int. Cl.[7] ............................. G01J 3/28; G01J 3/44; B24B 49/00
(52) U.S. Cl. ........................... 356/301; 356/326; 451/5; 451/6; 451/48
(58) Field of Search .................. 356/300, 301, 356/303, 326; 451/5, 6, 8, 9, 10, 48

(56) References Cited

U.S. PATENT DOCUMENTS

| | | | |
|---|---|---|---|
| 3,809,870 A | * | 5/1974 | Auble et al. |
| 4,563,897 A | * | 1/1986 | Moore |
| 4,786,220 A | | 11/1988 | Fildes et al. ................. 409/134 |
| 5,096,634 A | * | 3/1992 | Tsadares et al. |
| 5,155,773 A | | 10/1992 | Hansen |
| 5,189,625 A | | 2/1993 | Le Floch |
| 5,718,615 A | | 2/1998 | Boucher et al. ................ 451/5 |
| 5,929,986 A | | 7/1999 | Slater et al. ................. 356/326 |
| 5,934,974 A | | 8/1999 | Tzeng ............................ 451/6 |
| 6,033,288 A | | 3/2000 | Weisshaus et al. ............. 451/8 |

FOREIGN PATENT DOCUMENTS

| | | |
|---|---|---|
| DE | 270 142 A1 | 7/1989 |
| EP | 61252051 | 11/1986 |
| EP | 0 752 293 A2 | 1/1997 |
| JP | 5-148089 | * 6/1993 |
| JP | 9-85587 | * 3/1997 |
| WO | WO 98/08066 | 2/1998 |
| WO | WO 00/16036 | 3/2000 |

* cited by examiner

Primary Examiner—Ricky D. Shafer
(74) Attorney, Agent, or Firm—Robert I. King (57) ABSTRACT

A machining apparatus (10) comprises a material removing tool (12) movably mounted for removing material from a workpiece (14); means for illuminating (42, 54) a sample area upon a tool surface (34) with excitation radiation; means for receiving (42, 54) sample light emitted from the sample area; a spectral analyzer (54) for performing a spectral analysis of the sample light received; and means for determining (60) the condition of the tool at the sample area from the spectral analysis of the sample light. The wear of the tool (12) is determined as such a condition. Operation parameters of the machining apparatus (10) are adjusted according to the determined wear. An example application is a wafer dicing tool.

24 Claims, 5 Drawing Sheets

APPARATUS AND METHOD FOR MEASURING THE DEGRADATION OF A TOOL

FIELD OF THE INVENTION

The present invention generally relates to degrading tools, which wear during use.

BACKGROUND OF THE INVENTION

Equipment for mechanical machining a workpiece often uses degrading tools to remove material from a workpiece, for example cutting tools or abrasive tools such as lapping or grinding or polishing tools. Usually the work layer of the tool is of a harder material than the workpiece, but nevertheless it degrades over its lifetime. Non-optimal work conditions result in an extended machining time, in unnecessarily fast degradation of the tool, or in damage to the workpiece, all of which are economically unfavorable. Especially workpieces of a very hard material need very expensive tools. The actual optimal work condition depends on the actual condition criteria degradation of the tool.

U.S. Pat. No. 4,786,220 discloses a cutting tool wear monitor for detecting tool wear failure of a drill by monitoring a voltage or current which is generated between drill and workpiece during drilling. It is detected when the tool is worn out.

U.S. Pat. No. 5,934,974 describes In-situ monitoring of the wear of a polishing pad for polishing semiconductor wafers by laser triangulation. The polishing tool is adjusted to compensate uneven wear of the tool.

Both U.S. patents employ effects for the measurement, which are application specific. There is a further need for more general measuring the degradation of a tool.

Now, a special field of degrading tools, which wear during use is cutting (dicing) processed semiconductor wafers for die separation with blades, which wear during use. A processed semiconductor wafer has dies comprising electronic circuits thereupon in a rectangular pattern of rows and columns. These dies are separated by a dicing blade for packaging into single housings. Typically, the blade thickness ranges from 0.015 mm to 1.3 mm. The dicing blade comprises particles of diamond as typical abrasive material within a carrier material and cut the wafer with a liquid present for cooling and removing saw dust. Three types of dicing blades are commercially available:

Sintered Diamond Blade, in which diamond particles are fused into a soft metal such as brass or copper, or incorporated by means of a metallurgical process;

Plated Diamond Blade, in which diamond particles are held in a nickel bond produced by an electroplating process; and Resinoid Diamond Blade, in which diamond particles are held in a resin bond to create a homogeneous matrix.

Silicon wafer dicing is dominated by the plated diamond blade and the resinoid diamond blade. The resinoid diamond blade has the advantage that it is self-sharpening automatically by the cutting process.

Due to the abrasive nature of the process the dicing blade wears. A used-up or damaged dicing blade causes die damage as large particles break away from the die border. The operation parameters of the dicing blade are adjusted so that a suitable compromise of high throughput, small die damage level and reasonable blade wear is reached and usually left constant.

Usually, the dicing blade is either checked from time to time and exchanged when a certain degradation is reached, or it is exchanged after a defined number of wafers cut or a defined operation time. This conception can prevent die damage on the cost of labor for manual checking and/or too early exchange of the dicing blade, which means unnecessary blade costs and down time.

Several approaches have been undertaken to improve this compromise by detecting when the blade is considered used up. The detectable operational conditions according to the art are when the load induced on the blade by the wafer substrate reaches a predefined value or the when the blade cutting edge reaches a minimum separation distance from the work surface.

U.S. Pat. No. 6,033,288 discloses an apparatus for accumulating dicing data having a spindle motor, a spindle with a blade, a spindle driver to drive the spindle at a predetermined rotation rate, and a sensor connected to the spindle motor to determine the rotation rate of the spindle. A controller controls the spindle driver responsive to the load induced on the blade by the substrate.

According to U.S. Pat. No. 5,718,615 a semiconductor wafer dicing saw is controlled by monitoring blade exposure from a flange holding the blade during the wafer dicing process. A system measures the flange clearance using a height sensor to determine blade wear and a processor for monitors blade movement toward the wafer during the wafer dicing and stops the movement when the blade cutting edge reaches a minimum separation distance from the work surface.

Both conceptions provide unsufficient precision of the used-up condition of the blade.

DETAILED DESCRIPTION OF A PREFERRED EMBODIMENT

The present invention seeks to provide an apparatus and method for measuring the degradation of a tool and/or to detect when the tool is worn out. Further, the present invention seeks to provide a machine having a degrading tool, wherein machining parameters of the machine are controlled according to the determined condition of the tool, and a method therefore. Such apparatus and method allow to extend the lifetime of the tool and to reduce damage to a workpiece.

The wear of a material removing tool is accompanied by modified optical features of the material removing surface, i.e. work surface, of the tool. In accordance with the invention, these modifications of the optical features can be detected spectroscopically. Such optical features may show up and may be detected not only in the visual spectral range but also in neighboring spectral ranges of electromagnetic radiation including infrared and ultraviolet radiation.

Many material removing tools have a body giving structure to a work layer of the tool, which may comprise several distinct geometrical surfaces. The body provides form stability to the tool and the work layer interacts with the workpiece and comprises of or contains particles of an especially hard material. Commonly used materials for work layers are e.g. titanium nitride (TiN), cubic boron nitride (CBN) and diamond. For example surgical drills are made of surgical grade stainless steel or carbon steel coated by a thin layer of titanium nitride. Diamond is used in form of very small particles, which are embedded in a carrier material providing the work layer material. The carrier material is softer than the small diamonds and possibly also softer than the workpiece material. The carrier material on the work surface between the diamonds is abraded by the workpiece material, leaving the diamonds partly embedded and sticking out of the carrier material for removing the workpiece material. Such tools are widely used e.g. for stone saws and for semiconductor wafer backside polishing apparatuses.

For such tools, wear shows in a modified chemical composition of the work surface, which according to the invention is detectable by means of spectroscopy. Compared to a new tool comprising the chemical elements of the work surface, a tool in use comprises also a certain amount of atoms of the chemical elements of the workpiece. When the tool is worn out, i.e. the work layer is used up, the chemical elements of the tool body appear on the work surface. Thus, the wear of the tool is mapped in the ratio of chemical elements on the work surface and also in the optical features of the work surface.

According to the invention, the optical features of the work surface of a tool of a machining apparatus are detected spectroscopically. Further, the condition of the tool is determined from the optical features of its work surface. The condition of the tool contains at least one condition criteria of interest. Such condition criteria can be for example the wear of the tool, its tension or its temperature. The condition criteria can be quantified by a respective condition criteria value for each condition. For example, a condition criteria can be simply assume of the value good/bad to distinct between working tools and used up tools or can assume a range of numbers for finer specifying the degree of wear of a tool.

Also according to the invention, work parameters of the machining apparatus are determined with respect to the condition of the tool. Such work parameters can include the speed of moving parts and can be chosen to extend the lifetime of the tool, or to reduce the tension or the temperature of the tool.

The applicability of the invention is very broad and will be demonstrated by special examples representing applications showing different kinds of machining apparatus, different types of tools, different spectroscopes, and applications in different fields of the industry.

Figure 1:
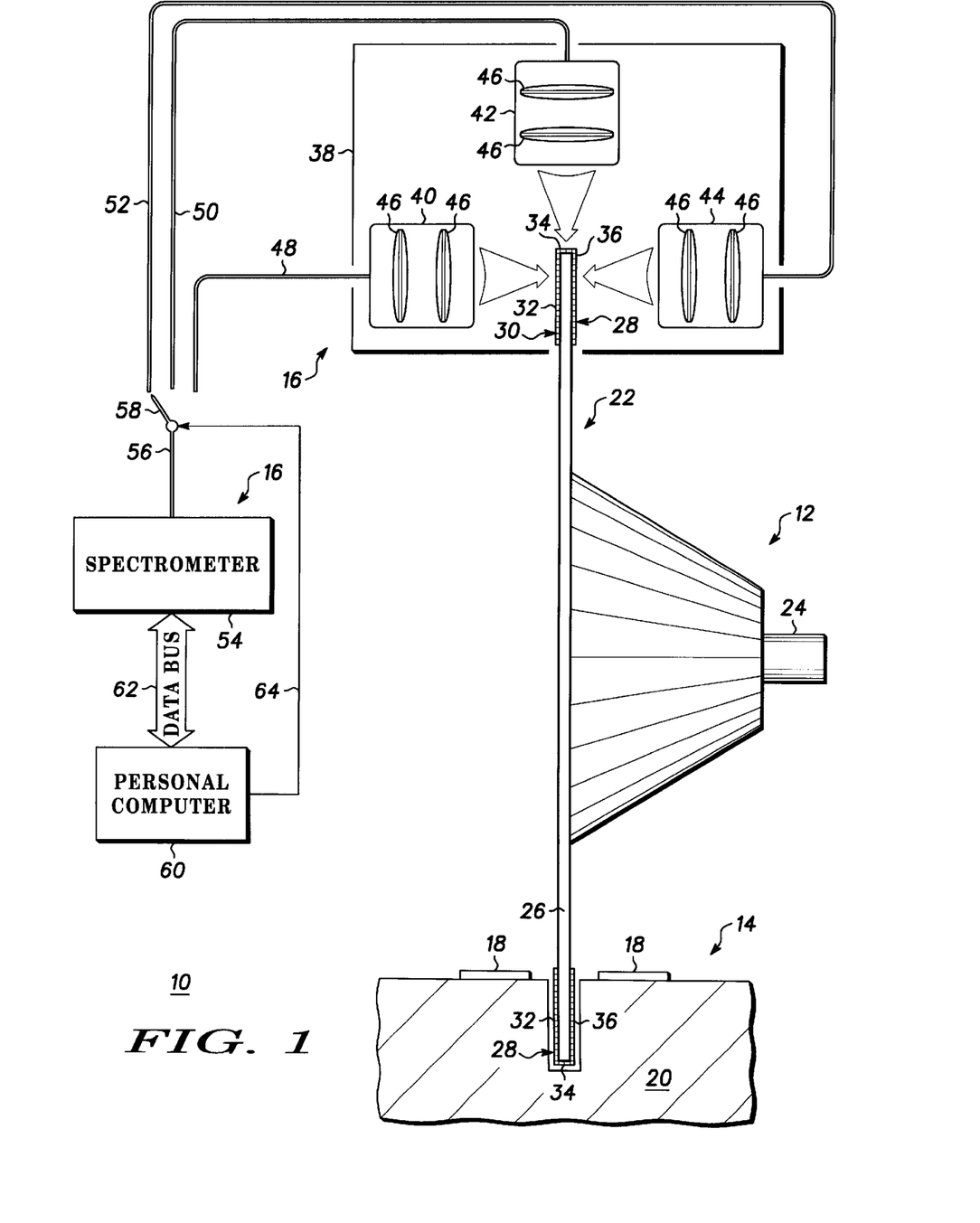
FIG. 1 is a schematic view of a cutting machine employing an apparatus according to an embodiment of the invention.

FIG. 1 shows schematically machining apparatus 10 having material removing tool 12 movably mounted for removing material from workpiece 14, and spectroscopic analyzer 16. Machining apparatus 10 is an wafer dicing apparatus used in the semiconductor industry for machining workpiece 14 which is here wafer 20, namely for separating integrated circuits 18 on wafer 20 into single chips which are packaged individually. Material removing tool 12 comprises so called dicing wheel 22 for dicing thin round wafer 20 rectangularity into single chips. Dicing wheel 22 is mounted on axis 24. Dicing wheel 22 has body 26 giving structure to work layer 28 at the circumference of dicing wheel 22. Work layer 28 comprises diamond particles embedded in a carrier material. Work surface 30 of work layer 28 is the material removing surface section of dicing wheel 22, which dices wafer 20. Here, work surface 30 comprises distinct geometrical surfaces 32, 34, 36, which are in abrasive contact with wafer 20. In this example, machining apparatus 10 has a fixed dicing wheel 22 and a movable slide (not shown) carrying wafer 20 moving the wafer along the direction of the dicing by a defined forward speed.

Spectroscopic analyzer 16 comprises detection head 38 having three microscope objectives 40, 42, 44 with lenses 46. Microscope objectives 40, 42, 44 are coupled to optical fibers 48, 50, 52, respectively. Microscope objectives 40, 42, 44 optically view or map defined sample areas of work surface 30 on geometrical surfaces 32, 34, 36, to optical fibers 48, 50, 52, respectively. When dicing wheel 22 is turning, the sample areas move along a path on geometrical surfaces 32, 34, 36. The area size of the sample areas is adjustable by adjusting microscope objectives 40, 42, 44.

Detection head 38 is a measurement head for determining the condition of degrading cutting edge of dicing wheel 22. Geometrical surfaces 34, 32, 36 of dicing wheel 22 form front face 34 and first and second side faces 32, 36 substantially rectangular to the front face. Microscope objectives 42, 40, 44 form guiding means for guiding illuminating radiation onto a sample area upon a tool surface and simultaneously form sample means for receiving sample light emitted from the sample area, one for each of the front and first and second side sections of the sample area. Detection head 38 is adapted to the dicing wheel 22 such that a front and first and second side sections of the sample area are upon the front and first and second side faces of dicing wheel 22, respectively. Microscope objectives 42, 40, 44 are adapted to optical fibers 50, 48, 52, respectively, one for each of the front and first and second side sections of the sample area. Detection head 38 forms a block-like measurement head in the meaning that its parts are readily calibrated with respect to each other such that the measurement head can be adjusted to dicing wheel 22 as one piece. Detection head 38 is adapted for receiving illuminating radiation via optical fibers 50, 48, 52 and for transmitting sample light via optical fibers 50, 48, 52. Such a block-like measurement head greatly improves the handling of the hole apparatus.

Spectroscopic analyzer 16 comprises Raman-spectrometer 54 coupled via optical fiber 56 to fiber selector 58. Fiber selector 58 is selectively coupled to one of optical fibers 48, 50, 52. Fiber selector 58 is a switch for selectively feeding sample light of a chosen sample area to the spectral analyzer. This allows to use one spectral analyzer, here the Raman-spectrometer, for several distinct sample areas and thus reduces the costs of the apparatus significantly. Raman-spectrometer 54 comprises a laser for illuminating the actual selected sample area on the tool surface with excitation radiation. Raman-spectrometer 54 is coupled via data bus 62 to personal computer (PC) 60. PC 60 is coupled via control line 64 to fiber selector 58.

In operation, the optical path between spectrometer and actual sample area is used in both directions. The illuminating light from the laser within Raman-spectrometer 54 is fed through optical fiber 56 and behind fiber selector 58, optical fiber 48, 50, or 52, and through the actual microscope objective 40, 42, or 44 to the sample area under inspection.

This light illuminates a sample area upon a tool surface 32, 34, or 36 with excitation radiation. Light emitted from the actual sample area is collected by the same microscope objective 40, 42, or 44 and is fed through optical fibers to Raman-spectrometer 54. Raman-spectrometer 54 performs a spectral analysis of the sample light received and provides spectral data of the sample area under inspection, i.e. Raman spectral data. PC 60 controls Raman-spectrometer 54 via data bus 62 and controls fiber selector 58 via control line 64. Raman-spectrometer 54 sends spectral data via data bus 62 to PC 60. PC 60 evaluates the spectral data and determines the condition of the tool at the sample area under inspection therefrom. PC 60 subsequently selects all sample areas by switching fiber selector 58 and determines the condition of the tool at all sample areas. Therefrom, PC 60 determines a total condition of the tool. The condition of the tool is qualified by at least one condition criteria and can be quantified by a respective condition criteria value for each condition criteria. A PC display shows the spectrum and the determined condition of the tool both at all sample areas and in total. Raman-spectrometer 54 contains also a camera, which can observe the sample area under inspection and whichs image can be displayed on a screen for visual checking.

Then, PC 60 uses the condition of the tool to determine optimal machining parameters of machining apparatus 10. PC 60 controls machining apparatus 10 to implement the determined optimal machining parameters. Here, the optimal machining parameters include the forward speed of the slide and the rotation frequency of dicing wheel 22. PC 60 is programmed to determine the optimal machining parameters of machining apparatus 10 from condition criteria values representing the total condition of the tool according to a defined functional relationship. PC 60 is also programmed to detect differences in the condition of the tool between sample areas on geometrical surfaces 32 and 36 above a predetermined warning level. If such differences are detected, a misalignment error between wheel and slide is assumed and an error procedure is initiated. A PC display shows the determined optimal machining parameters of machining apparatus 10, and indicates visually and audibly if a condition criteria value of the tool is above a predetermined warning level.

Figure 2:
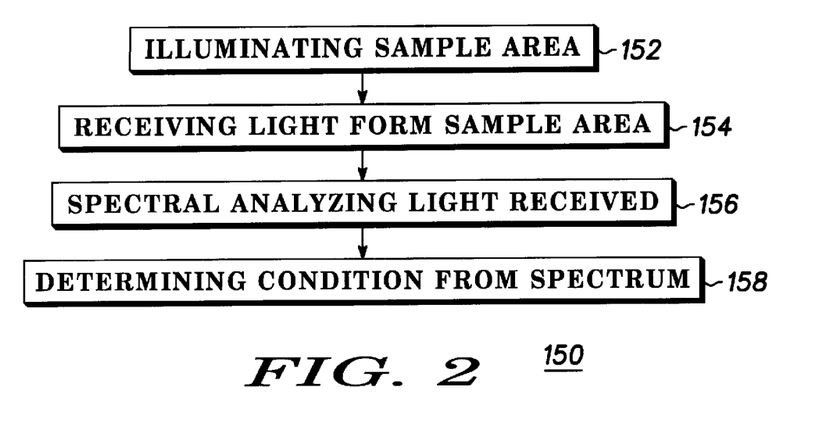
FIG. 2 is a flow diagram of a method according to an embodiment of the invention.

FIG. 2 shows of a method for determining the condition of a degrading tool according to an embodiment of the invention. This method comprises step 152 illuminating a sample area upon a tool surface with excitation radiation. Then in step 154 sample light emitted from the sample area is received. In step 156 the received sample light is spectrally analyzed. From the spectrum of the received sample light, the condition of the tool at the sample area is determined in step 158. The determined condition of the tool can be displayed or can be used to provide a warning signal if it is bad. The excitation radiation is chosen suitable such that its emission from the sample area is significantly dependent on the condition of the tool with respect to at least one condition criteria. Examples of such dependency is given below.

Figure 3:
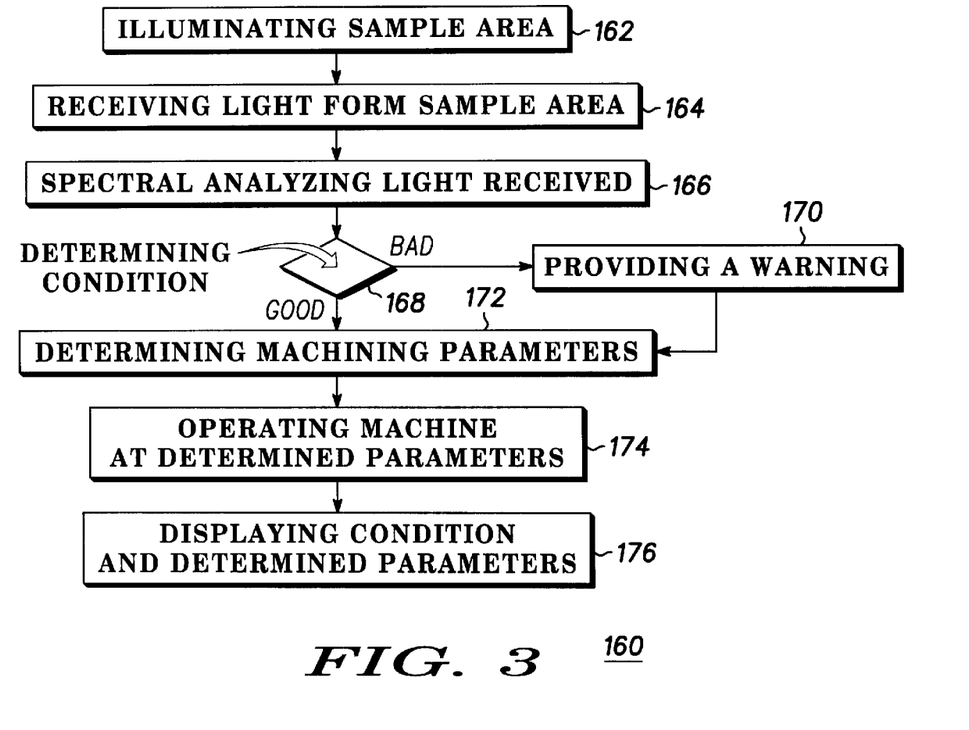
FIG. 3 is a flow diagram of a method according to another embodiment of the invention.

FIG. 3 shows flow diagram 160 of a method for controlling a machine having a degrading tool according to an embodiment of the invention. In step 162 a sample area upon a tool surface is illuminated with excitation radiation. In step 164 sample light emitted from the sample area as a result of the excitation is received. The received sample light is spectrally analyzed in step 166. From the spectrum of the received sample light, the condition of the tool at the sample area is determined in step 168. Here, this determining includes comparing a value representing the condition with a predetermined value. If the determined value is worse than the predetermined value then a warning is provided, step 170. Next, in both cases with or without warning, machining parameters of the machine are determined dependent on the determined condition of the tool, step 172. Then, step 174, the tool is operated with the determined machining parameters. Additionally, the determined condition of the tool and the determined machining parameters are displayed, step 176.

Preferably, the wear of the tool is a condition criteria quantified with a condition criteria value, which changes significantly during the lifetime of the tool. This change in the condition criteria value is evaluated from the spectrum of the received light according to a predetermined function. Another predetermined function is used to determine machining parameters of the machine which are optimized for a long lifetime of the tool and minimum damage to the workpiece according to the actual condition, here wear, of the tool. Both predetermined functions can be combined to one resulting function such that the condition criteria value doesn't show up explicitly, but this is nevertheless understood as including determining the condition of the tool.

Those skilled in the art will know that all computing and controlling of the machine can be performed by a single computer such as a PC or an integrated microprocessor within the machine. This includes performing a spectral analysis, computing condition criteria values, computing optimal machining parameters and controlling the machine, running machining application programs, etc. Usually a spectrometer is computer controlled and this computer can take additional tasks of controlling the machine.

Currently, many machining apparatuses are operating a tool at a constant standard speed. Evaluation of many dicing and sawing situations have shown that a new sawing wheel or dicing wheel can advantageously be operated at a beginning speed greater than a standard speed for a short time, at the standard speed for a long time, and a reduced speed relative to the standard speed at the end of lifetime of the wheel with respect to the workpiece.

Here, during the lifetime of dicing wheel 22 work layer 28 will degrade and thus work surface 30 will change its condition. The carrier material of work layer 28 is softer than the small diamonds and also softer than the workpiece material of wafer 20. The carrier material on work surface 30 between the diamonds is abraded by the workpiece material, leaving the diamonds partly embedded and sticking out of the carrier material for removing the workpiece material. Diamonds show a certain size distribution and can be unevenly distributed in the work layer. During use and wear, diamonds can stick out of the carrier material unevenly and can be more or less strongly fixed within the carrier material. Such non-uniformities and mechanical imperfections of machining apparatus 10 as bearing and non-exact positioning of dicing wheel 22 contribute to a non-uniform material removal over the circumference of dicing wheel 22 during one turn. The non-uniform material removal can lead to damage to both wafer 20 and dicing wheel 22. Damage to wafer 20 includes chipping, i.e. breaking portions out of the wafer, which are much bigger than the size of the outsticking diamonds, and breaking of the wafer. Damage to dicing wheel 22 includes breaking portions out of work layer 28 which are much bigger than the size of the outsticking diamonds. Damage is done also by secondary effects due to temperature rising at the dicing track in both wafer 20 and dicing wheel 22.

From a different point of view, the condition of dicing wheel 22 changes during wear. Such condition can include condition criteria position of the actual work surface 30, thickness, degradation, temperature and contamination by small particles of work layer 28. These changed condition of a used dicing wheel is typically worse than the condition of a new wheel with respect to cutting efficiency. According to the invention, the machining parameters of the machining apparatus such as rotational speed of the dicing wheel and speed of linear movement of the wafer relative to the wheel are set to a values optimized for the actual state of degradation. The cutting efficiency, the risk of wafer damage, and the lifetime of the tool can be greatly improved by adjusting the machining parameters of the machining apparatus to the actual condition of the tool.

For such tools, wear shows in a modified chemical composition of the work surface, which according to the invention is detectable by means of spectroscopy. Compared to a new tool comprising the chemical elements of the work surface, a tool in use comprises also a certain amount of atoms of the chemical elements of the workpiece. When the tool is worn out, i.e. the work layer is used up, the chemical elements of the tool body appear on the work surface. Thus, the wear of the tool is mapped in the ratio of chemical elements on the work surface and also in the optical features of the work surface. The condition of the tool may include condition criteria that are depending on the actual load such as temperature or stress. Any condition criteria which shows in the spectrum is observable. Especially, the Raman spectrum information preferably contains at least one of the group intensity, position, polarization, and widths of Raman spectral lines. The distance of a Raman spectral line from the excitation frequency is characteristic for the surface material substance or chemical composition and the stress. Thus contamination by small particles of a known substance as well as the appearance of dicing wheel carrier material on the work layer are detectable therewith. In particular, burning of the diamond dicing material due to insufficient cooling of the dicing blade gives rise to additional graphite signals in the Raman spectrum, which can be discriminated from the diamond signal. The polarization of light from a Raman spectral line is dependent on mechanical stress that applies to the tool. Thus critical loads of the tool can be detected therewith.

In FIG. 1, the number of three microscope objectives 40, 42, 44 in detection head 38 has been chosen to observe sample areas on three geometrical surfaces 32, 34, 36, respectively. The number of sample areas may vary with the number of geometrical surfaces or other application specifics. One sample area and one light collecting element can be sufficient.

Figure 4:
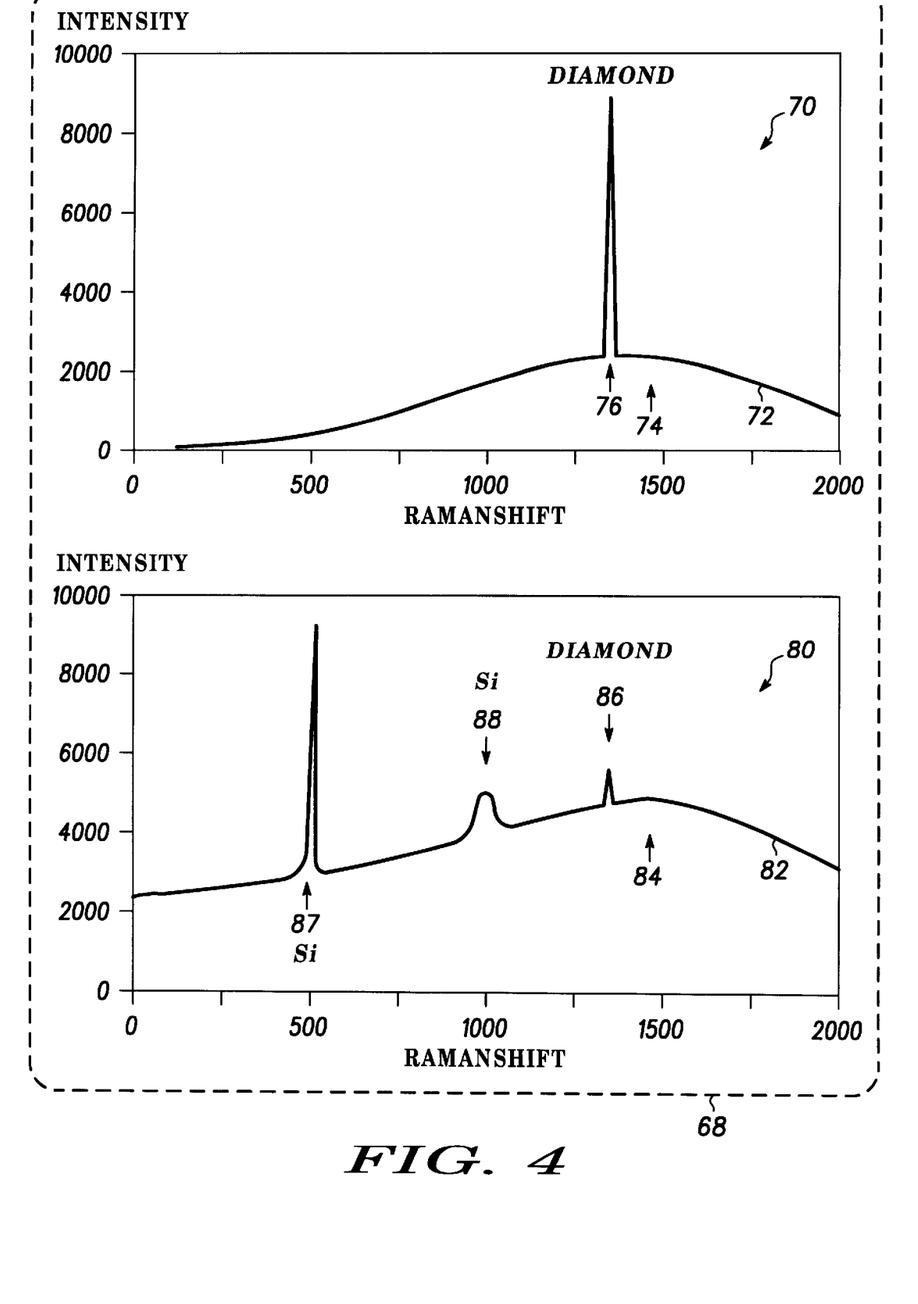
FIG. 4 shows diagrams of measurements by the machine of FIG. 1.

FIG. 4 shows diagrams of Raman measurements 68 by the machine of FIG. 1, namely Raman spectrum 70 of a new dicing wheel, and Raman spectrum 80 of a used dicing wheel near the end of it's lifetime. Raman spectrum 70 shows the intensity as function of the Ramanshift, which is the spectral distance of the observation wavelength from the excitation wavelength. Spectrum 70 shows ground line 72 having broad maximum 74 and peak line 76. Peak line 76 is a narrow Raman spectral line characteristic for diamond. The intensity ratio between the maximum of peak line 76 and broad maximum 74 is a measure of the amount of diamond particles at the area of observation at the surface of the dicing wheel.

Raman spectrum 80 shows the intensity as function of the Ramanshift. Spectrum 80 shows ground line 82 having broad maximum 84 and peak line 86 characteristic for diamond. Peak line 86 shows a comparatively small maximum because not many diamond particles are left on the surface of the dicing wheel. Additionally, peak lines 87 and 88 both characteristic for silicon rise significantly from ground line 82. This shows contamination from silicon particles on the dicing wheel. The ratio between the maximum of peak line 86 characteristic for diamond and the maximum of peak line 87 characteristic for silicon is a measure of the condition of the dicing wheel.

Figure 5:
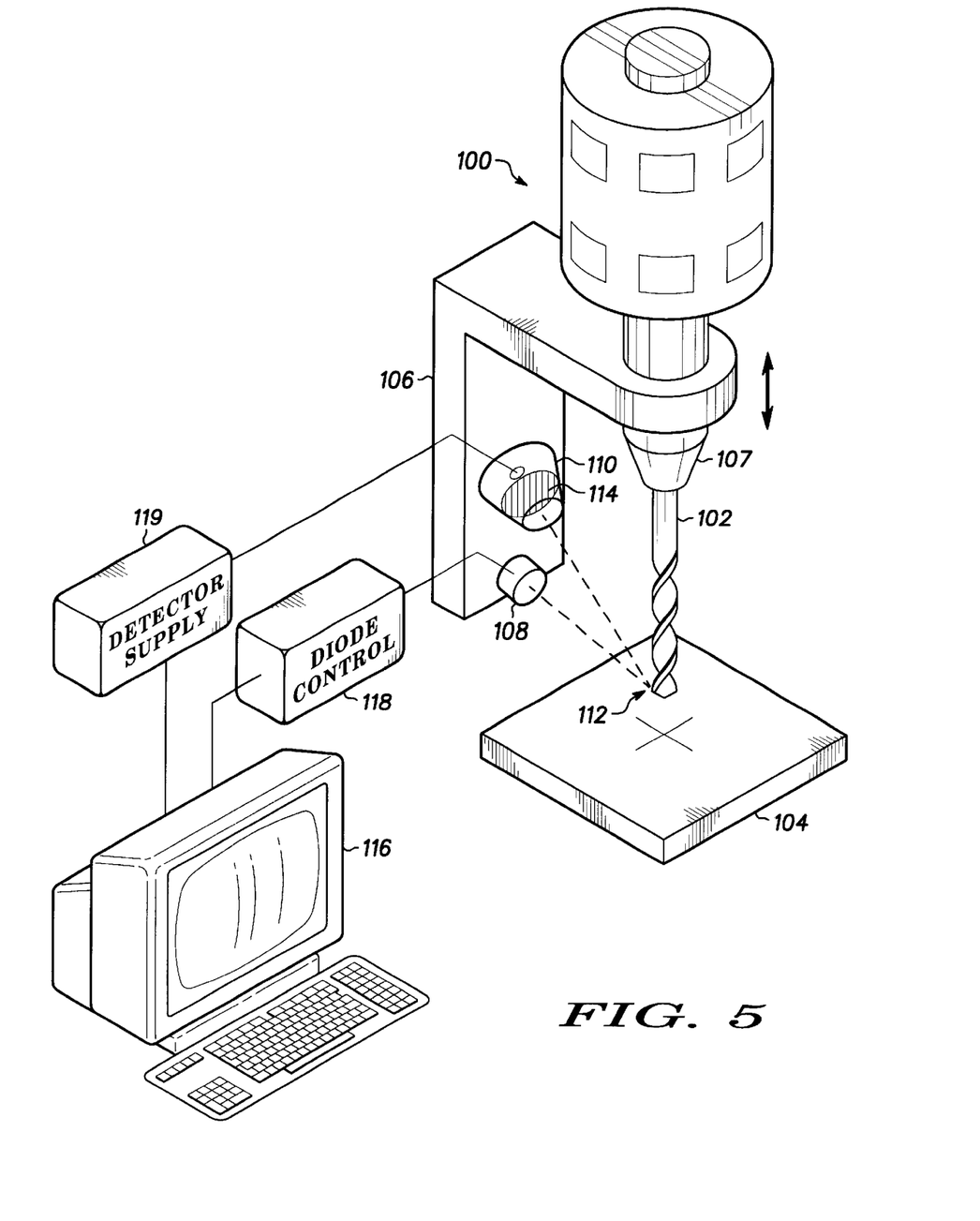
FIG. 5 is a schematic view of a drilling machine employing an apparatus according to an embodiment of the invention.

FIG. 5 shows schematically drilling machine 100 employing an apparatus according to an embodiment of the invention employing classical spectroscopy. Drilling machine 100 has drill 102 for drilling workpiece 104. Drill 102 is the degrading tool under observation. Drilling machine 100 has further drill frame 106 supporting drill head 107 which rotates and chucks drill 102. Drill frame 106 moves to and from workpiece 104 together with drill 102. Drill frame 106 carries laser diode unit 108 and photodetector 110. Laser diode unit 108 illuminates an area of observation 112 on the surface of the tip of drill 102. Preferably, the cutting edge of drill 102 moves within area of observation 112. Photodetector 110 collects and receives light emitted from area of observation 112. Photodetector 110 has filter 114 for performing spectral analysis of light received. PC 116 controls laser diode unit 108 via diode control 118. PC 116 receives a signal from photodetector 110 via detector supply 119.

Drill 102 is surface coated with a hard material. Controlled by PC 116, laser diode unit 108 illuminates area of observation 112 with excitation light of a suitable predetermined excitation frequency. Photodetector 110 receives filtered reflected excitation light from the area of observation 112 but suppresses stray light. Filter 114 is chosen with respect to the hard material of the surface coating of drill 102 and to the carrier material of drill 102. For the excitation light the hard material of the surface coating of drill 102 has a high reflection coefficient and the carrier material of drill 102 has a small reflection coefficient. PC 116 acts as a comparator comparing the signal received from photodetector 110 to a predetermined value. When the surface coating is used up, the light received by photodetector 110 and thus the signal received by PC 116 decreases significantly and PC 116 provides a warning signal.

The invention is not limited to dicing, sawing, and cutting but also applicable to other abrasive machining including grinding and polishing.

Figure 6:
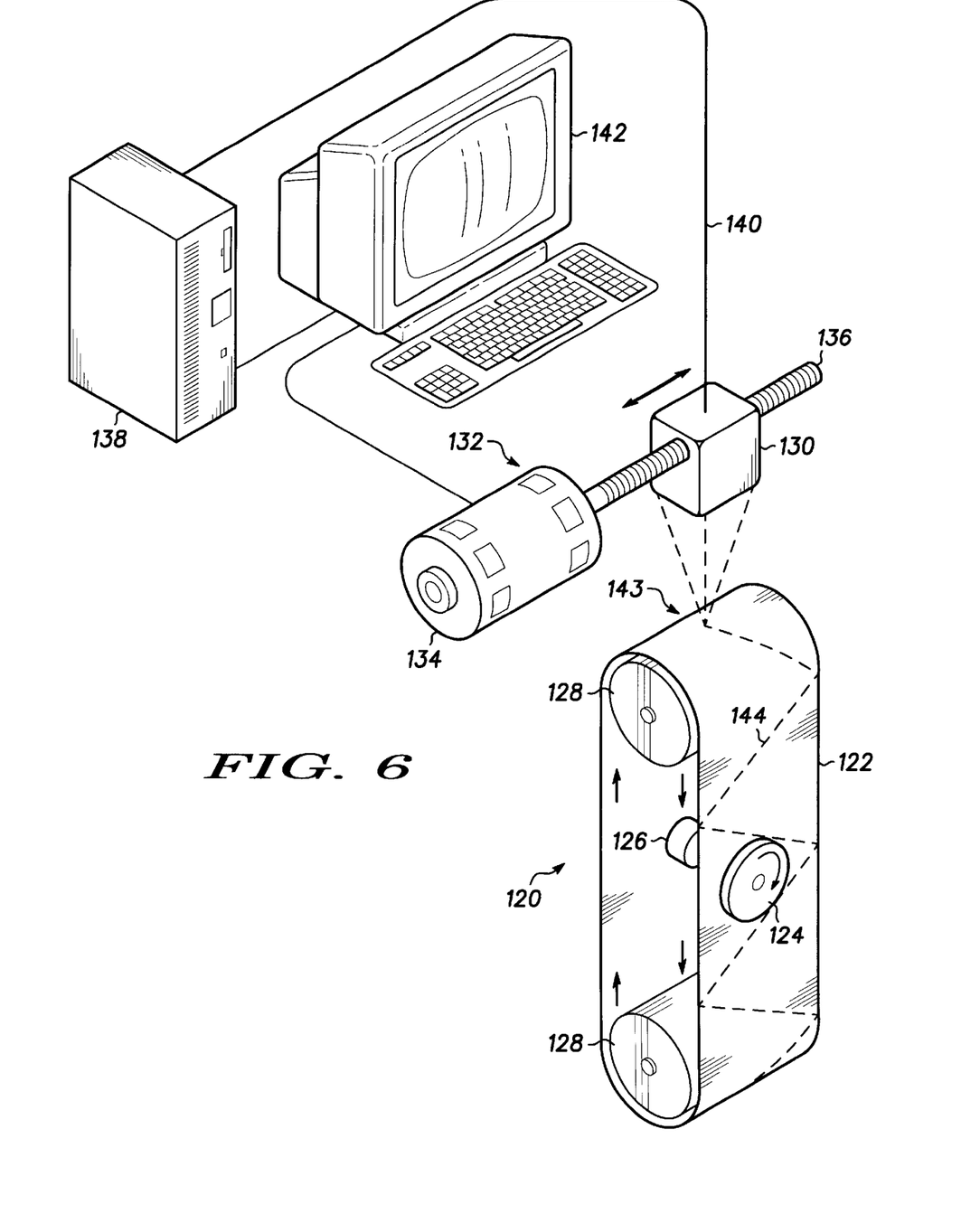
FIG. 6 illustrates schematically a polishing machine employing an apparatus according to an embodiment of the invention.

FIG. 6 shows polishing machine 120 in accordance with an embodiment of the invention. Polishing machine 120 is a CMP machine for chemical mechanical polishing a semiconductor wafer. Polishing machine 120 includes a degrading tool consisting of belt 122 carrying polishing pads. Further, polishing machine 120 includes wafer carrier head 124 that positions the wafer against the polishing pads, support bearing 126 that supports belt 122 under wafer carrier head 124, a belt drive system including rollers 128 to move belt 122 and the polishing pads, and optical head 130 mounted on sensor drive system 132 that includes drive motor 134 and drive spindle 136. Optical head 130 is the optical head of Raman-spectrometer 138 and coupled thereto by optical fiber 140. PC 142 controls Raman-spectrometer 138 and drive motor 134.

In operation, the belt drive system rotates belt 122 so that the polishing pads slide past an exposed surface of a wafer mounted on wafer carrier head 124. Support bearing 126 and wafer carrier head 124 co-operate to keep the polishing pads parallel to and uniformly in contact with the surface of the wafer. Raman-spectrometer 138 comprises a laser illuminating sample area 143 on the tool surface with excitation radiation via optical fiber 140 and optical head 130. Sample area 143 moves along on belt 122 on path 144 in zigzag form resulting from the movement of belt 122 and optical head 130 moved by drive spindle 136. Raman light emitted from sample area 143 is collected by optical head 130 and via optical fiber 140 transmitted to Raman-spectrometer 138. PC 142 controls Raman-spectrometer 138, which provides spectral data to PC 142. PC 142 determines the condition of the tool at sample area 143 as it moves along path 144, quantifies the degradation at sample area 143 as one condition criteria, and maps the determined condition with respect to the position of sample area 143 upon belt 122. A PC display shows the degradation of the tool at its different areas. A warning message is displayed if the degradation of the tool is too unevenly distributed over the belt surface or if the degradation of the tool has reached a predefined value.

Those skilled in the art know further that a more simple machine can make use of the invention by employing a comparator for determining the condition of the tool. Such simple machine can just distinct between the tool being good or bad by observing a spectral feature and comparing it's value to a predetermined value. For example an ordinary non-Raman-spectroscope can consist of a lamp for illuminating a sample area upon the tool surface with excitation radiation, a photodetector for receiving sample light emitted from the sample area, a spectral filter for performing a spectral analysis of the sample light received, and a comparator. The comparator determines the condition of the tool at the sample area from the spectrally filtered sample light. The condition of the tool is good if the photodetector signal is lower or bad if it is higher than a predetermined value. With a suitable spectral filter, the apparatus detects when material of the wheel body appears on the surface of the working layer and provides a warning signal that the tool is used up.

While the invention has been described in terms of particular structures, devices and methods, those of skill in the art will understand based on the description herein that it is not limited merely to such examples and that the full scope of the invention is properly determined by the claims that follow.

What is claimed is:

1. An apparatus for determining an operating condition of a semiconductor cutting tool having at least one condition criteria comprising:

first means for illuminating a first sample area upon a tool surface with excitation radiation;

first means for receiving first sample light emitted from the first sample area;

a spectral analyzer for performing a spectral analysis of the first sample light received; and computer means coupled to the spectral analyzer for determining the operating condition of the tool at the first sample area from the spectral analysis of the first sample light, the computer means using the operating condition of the semiconductor cutting tool at the first sample area to determine at least one of a speed that the semiconductor cutting tool is to be operated at and a speed of linear movement of a semiconductor relative to the semiconductor cutting tool.

2. The apparatus of claim 1, wherein the spectral analyzer is a Raman spectral analyzer for providing Raman spectrum information of the first sample light.

3. The apparatus of claim 2, wherein the Raman spectrum information contains at least one of: intensity, position, polarization, and widths of Raman spectral lines.

4. The apparatus of claim 1, wherein the operating condition of the semiconductor cutting tool comprises at least one condition criteria of the group consisting of degradation, temperature and contamination by small particles.

5. The apparatus of claim 1, wherein the first means for receiving comprises an objective for collecting the first sample light emitted from the first sample area and an optical fiber.

6. The apparatus of claim 1, further comprising:

second means for illuminating a second sample area upon a tool surface with excitation radiation; and second means for receiving second sample light emitted from the second sample area and coupled to the spectral analyzer for performing a spectral analysis of the second sample light received, wherein the computer means determines the operating condition of the tool at the second sample area from the spectral analysis of the second sample light.

7. The apparatus of claim 1, wherein the tool is moving and the first sample area is moving along a surface of the tool.

8. The apparatus of claim 1, wherein the semiconductor cutting tool is a wheel-like cutting tool.

9. The apparatus of claim 1, wherein the semiconductor cutting tool is a diamond embedded dicing wheel.

10. The apparatus of claim 1, wherein the computer means provides a warning signal when a predetermined condition criteria value is reached.

11. A machining apparatus comprising a semiconductor wafer cutting tool movably mounted for separating integrated circuits from a wafer;

means for illuminating a sample area upon a tool surface with excitation radiation;

means for receiving sample light emitted from the sample area;

a spectral analyzer for performing a spectral analysis of the sample light received; and computer means for determining a condition of the tool at the sample area from the spectral analysis of the sample light, the computer means using the condition of the tool at the sample area to determine an optimal separation parameter of the machining apparatus and operating the machining apparatus at the optimal separation parameter.

12. The machining apparatus of claim 11 wherein the tool is a wheel-like cutting tool and the separation parameter is a speed of rotation of the wheel-like cutting tool.

13. A method for determining an operating condition of a semiconductor cutting tool comprising:

illuminating a first sample area upon a tool surface with excitation radiation;

receiving first sample area light emitted from the first sample area;

spectral analyzing the first sample area light received;

determining with a computer the operating condition of the tool at the first sample area from the spectrum of the first sample area light and adjusting a cutting speed of the semiconductor cutting tool in response thereto.

14. The method of claim 13, wherein the spectral analyzing is performed by a Raman spectrometer.

15. The method of claim 14, wherein the first sample area light contains information about intensity, position, polarization, and widths of Raman spectral lines.

16. The method of claim 13, wherein the operating condition of the tool comprises at least one condition criteria of the group consisting of degradation, temperature and contamination by small particles.

17. The method of claim 16, wherein the tool is moving and the first sample area is moving along a surface of the tool.

18. The method of claim 16, wherein the tool is a wheel-like cutting tool.

19. The method of claim 16, wherein the tool is a diamond embedded dicing wheel tool.

20. The method of claim 16, wherein the computer provides a warning signal when a predetermined condition criteria value is reached.

21. The method of claim 13, further comprising:
illuminating a second sample area upon a tool surface with excitation radiation;
spectral analyzing second sample area light emitted from the second sample area; and
determining the operating condition of the tool at the second sample area from the spectrum of the second sample area light.

22. A method for controlling a machine having a semiconductor cutting tool comprising the steps:
determining a condition of the semiconductor cutting tool by illuminating a first sample area upon a tool surface with excitation radiation;
receiving first sample light emitted from the first sample area;
spectral analyzing the first sample light received;
continuously monitoring with a computer the condition of the tool at the first sample area from the spectrum of the first sample light;
determining machining parameters of the machine dependent on the determined condition of the tool including a speed of the semiconductor cutting tool; and
adjusting the speed of the semiconductor cutting tool to operate the tool with the determined machining parameters to make cuts in a semiconductor wafer between two integrated circuits.

23. A measurement head for determining a condition of a degrading edge of a wheel-like tool having a front face and first and second side faces substantially rectangular to the front face, comprising:
guiding means for guiding illuminating radiation onto a sample area upon a tool surface;
sample means for receiving sample light emitted from the sample area; wherein the measurement head is adapted to the wheel-like tool such that a front and first and second side sections of the sample area are upon the front and first and second side faces of the wheel-like tool, respectively; and
a computer coupled to the sample means for determining the condition of the degrading edge of the wheel-like tool at the sample area from spectral analysis of the sample light, the computer using the condition of the wheel-like tool at the sample area to determine an optimal operating parameter of the wheel-like tool and to adjust the optimal operating parameter according to the condition which was determined.

24. The measurement head of claim 23, wherein the guiding means further comprise three microscope objectives, one for each of the front and first and second side sections of the sample area.

* * * * *